United States Patent [19]

Fujisaki et al.

[11] Patent Number: 4,598,150
[45] Date of Patent: Jul. 1, 1986

[54] CHROMOGENIC 1-(3-METHOXY-4-ALKOXYPHENYL)-2-(2'-QUINOLYL)ETHYLENE COMPOUNDS

[75] Inventors: Hideaki Fujisaki, Kyoto; Seiichi Nieda, Uji; Katsuhiko Tsunemitsu, Kyoto, all of Japan

[73] Assignee: Yamada Chemical Co. Ltd, Kyoto, Japan

[21] Appl. No.: 580,604

[22] Filed: Feb. 16, 1984

[30] Foreign Application Priority Data

Feb. 18, 1983 [JP] Japan .................. 58-27142

[51] Int. Cl.$^4$ ........................... C07D 215/14
[52] U.S. Cl. ...................... 546/152; 546/178; 546/180
[58] Field of Search .......... 546/152, 178, 180

[56] References Cited

FOREIGN PATENT DOCUMENTS 21033 12/1966 Japan .
27169 8/1976 Japan .
58-25317 2/1983 Japan .

OTHER PUBLICATIONS

Chem. Abst. 99 (2), 6534t (1981), of Japanese Pat. No. 58/25317.
Beilsteins Handbuch Der Organischen Chemie, Zwanzigster Band, pp. 500 and 501.
Beilsteins Handbuch Der Organischen Chemie, Einundzwanzigster Band, pp. 194 and 193.
Beilsteins Handbuch Der Organischen Chemie, Zweites Erganzungswerk, Einundzwanzigster Band, pp. 94, 151, 152 and 173.

Lynch et al., "Kinetis of Styrylquinoline Formation", J. of Heterocyclic Chemistry, 1972, 9(4), pp. 789-799.
Tak et al; "Influence of Solvent Interaction on the Absorption Spectra of Some Phenol Betaines. Part II.", J. Indian Chem. Soc., vol. 49, No. 2, 1972, pp. 139-144.

Primary Examiner—Richard L. Raymond
Assistant Examiner—D. B. Springer
Attorney, Agent, or Firm—Cushman, Darby & Cushman

[57] ABSTRACT

The present invention relates to a novel compound of the formula:

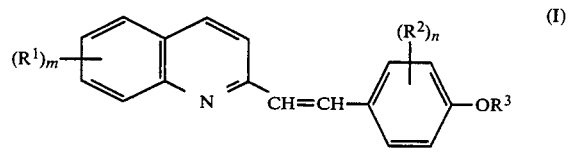

wherein $R^1$ and $R^2$ respectively represent hydrogen atom, lower alkyl group of 1 to 5 carbon atoms, lower alkoxy group of 1 to 5 carbon atoms or halogen atom; $R^3$ represents hydrogen atom, alkyl group of 1 to 12 carbon atoms, alkoxyalkyl group of 1 to 12 carbon atoms, halogenoalkyl group of 1 to 12 carbon atoms, phenyl group which may be substituted or benzyl group which may be substituted; and m and n are an integer of 1 or 2; providing the $R^1$ and $R^2$ do not represent hydrogen atom, methyl group and methoxy group when $R^3$ represents hydrogen atom or methyl group.

Further, the present invention relates to color developing compositions suitable for use in a recording material and pressure- or heat-sensitive recording sheet containing the novel compound of the formula (I).

2 Claims, 5 Drawing Figures

CHROMOGENIC 1-(3-METHOXY-4-ALKOXYPHENYL)-2-(2'-QUINOLYL)ETHYLENE COMPOUNDS

The present invention relates to novel chromogenic compound, color developing compositions suitable for use in a recording material and pressure- or heat-sensitive recording sheet containing the same.

Heretofore, yellowish color developing agents have been variously proposed and they are roughly classified into the following two groups.

Group 1. Yellowish color developing agents having lactone ring within their molecules:
(i) fluoran derivatives such as 3,6-dialkoxyfluoran (refer to Japanese Patent Publication No. 4698/1970 and No. 16053/1971) and 3-N-alkylaminofluoran (refer to Japanese Patent Publications No. 22650/1971 and No. 4051/1973),
(ii) chromenopyrazole compound (refer to Japanese Patent Publication No. 23513/1971),
(iii) aminophthalide compound (refer to Japanese Patent Application Laying-Open No. 111528/1979), and
(iv) acyloxytetrachlorophthalide (refer to Japanese Patent Publication No. 25654/1970).

Group 2. Yellowish color developing agents having no lactone ring within their molecules:
(i) spiropyrane derivative (refer to Japanese Patent Publications No. 10075/1971 and No. 11113/1971),
(ii) styryl compound (refer to Japanese Patent Publications No. 21033/1966 and No. 27169/1976),
(iii) pyridine derivative (refer to Japanese Patent Publication No. 9127/1978),
(iv) monomethine compound (refer to Japanese Patent Application Laying-Open No. 23406/1977 and Japanese Patent Publication No. 5929/1974), and
(v) benzopyrane compound (refer to Japanese Patent Publication No. 19274/1981).

In general, although the compounds of Group 1 having lactone ring within their molecule are generally low in spontaneous color-development when a solution thereof is placed on a sheet of paper and many of them are easily soluble in solvents, they have the demerits that the color-density is low and the developed color image is poor in lightfastness.

On the other hand, in general, the compounds of Group 2 having no lactone ring within their molecule have a high color density and the developed color image is excellent in lightfastness, however, they also have demerits that the solubility of them is poor, the solution thereof spontaneously develops color on a sheet of paper and they easily sublime.

It is an object of the present invention to provide novel compounds of the formula:

wherein $R^1$ and $R^2$ respectively represent hydrogen atom, lower alkyl group of 1 to 5 carbon atoms, lower alkoxy group of 1 to 5 carbon atoms or halogen atom; $R^3$ represents hydrogen atom, alkyl group of 1 to 12 carbon atoms, alkoxyalkyl group of 1 to 12 carbon atoms, halogenoalkyl group of 1 to 12 carbon atoms, phenyl group which may be substituted or benzyl group which may be substituted; and m and n are an integer of 1 or 2; providing that $R^1$ and $R^2$ do not represent hydrogen atom, methyl group and methoxy group when $R^3$ represents hydrogen atom or methyl group.

A further object is to provide color developing compositions suitable for use in a recording material, comprising at least one chromogenic compound as a color former of the formula:

wherein $R^1$ and $R^2$ respectively represent hydrogen atom, lower alkyl group of 1 to 5 carbon atoms, lower akoxy group of 1 to 5 carbon atoms or halogen atom; $R^3$ represents hydrogen atom, alkyl group of 1 to 12 carbon atoms, alkoxyalkyl group of 1 to 12 carbon atoms, halogenoalkyl group of 1 to 12 carbon atoms, phenyl group which may be substituted or benzyl group which may be substituted; and m and n are an integer of 1 or 2; providing that $R^1$ and $R^2$ do not represent hydrogen atom, methyl group and methoxy group when $R^3$ represents hydrogen atom or methyl group,
and an electron-accepting substance.

Other object of the present invention is to provide pressure- or heat-sensitive recording sheets, comprising microcapsules containing at least one chromogenic compound of the formula:

wherein $R^1$ and $R^2$ respectively represent hydrogen atom, lower alkyl group of 1 to 5 carbon atoms, lower alkoxy group of 1 to 5 carbon atoms or halogen atom; $R^3$ represents hydrogen atom, alkyl group of 1 to 12 carbon atoms, alkoxyalkyl group of 1 to 12 carbon atoms, halogenoalkyl group of 1 to 12 carbon atoms, phenyl group which may be substituted or benzyl group which may be substituted; and m and n are an integer of 1 or 2; providing that $R^1$ and $R^2$ do not represent hydrogen atom, methyl group and methoxy group when $R^3$ represents hydrogen atom or methyl group,
said chromogenic compound as a color former being dissolved in an organic solvent in said microcapsules.

Still other objects and advantages of the present invention will become apparent hereinafter.

The compounds of the present invention are almost colorless in itself. When the compounds of the present invention are brought into contact with an electron-accepting substance, the compounds are rapidly developed into yellowish color and accordingly, the compounds of the present invention are useful as a color developing agent for use in pressure-sensitive recording (or copying) paper or heat-sensitive recording paper.

The compounds of the present invention are superior to the conventional yellow color developing agents in the following points:

(1) higher in the color density and more stable to light,
(2) more easily soluble in organic solvents,
(3) smaller in spontaneous color-development when the solution thereof is placed on a sheet of paper, and
(4) more hardly sublimable.

As shown in Table 1, the compounds of the present invention are superior in color density and lightfastness to the comparative compounds described in Japanese Patent Publication No. 27169/1976.

TABLE 1

Figure 1:
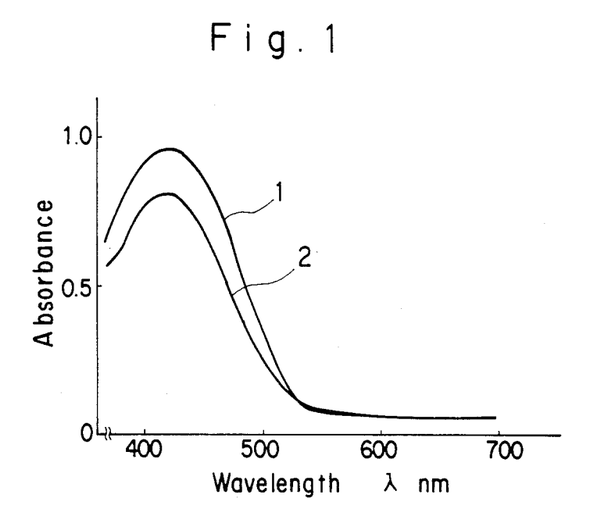
FIGS. 1 and 2 respectively show the curve of color density of Compound Nos. 1 and 6 of the present invention, and FIGS. 3, 4 and 5 respectively show the curve of color density of Comparative compound Nos. 1, 2 and 3 described in the prior art publication. Curve 1 shows the color density of the developed compound just after developing and Curve 2 shows the color density of the developed compound when the developed compound is exposed to direct sunlight for 4 hours after developing the compound.
Figure 2:
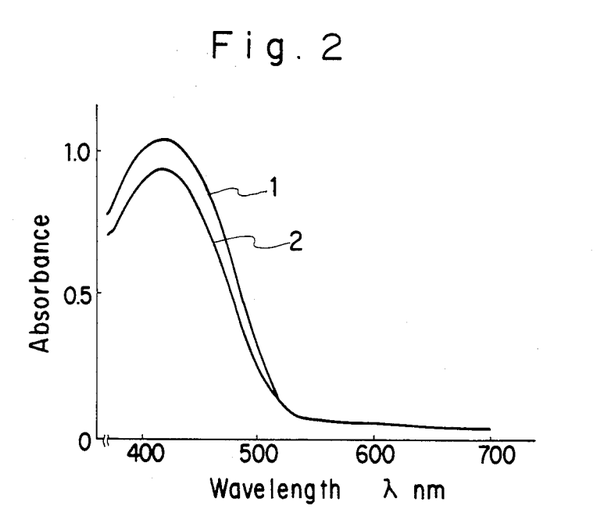
Figure 3:
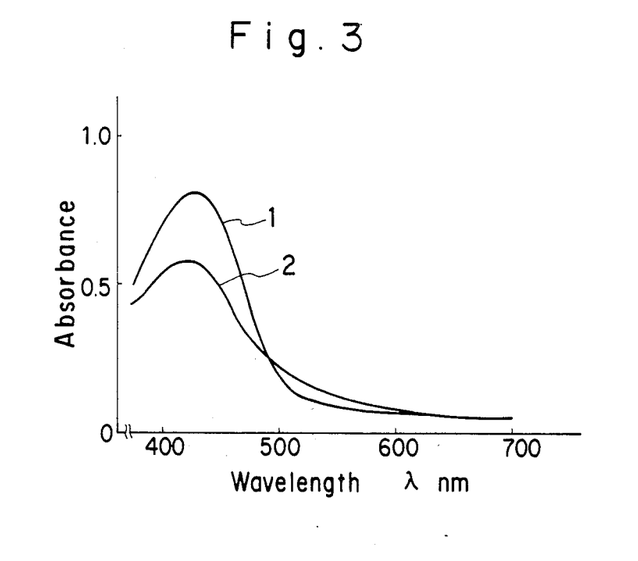
Figure 4:
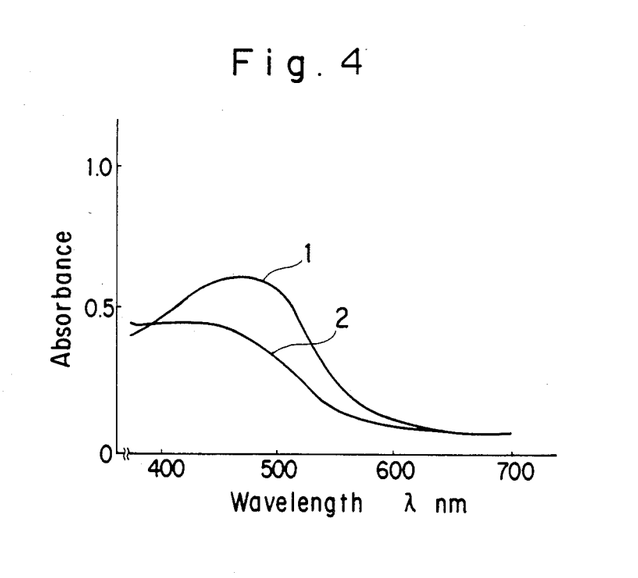
Figure 5:
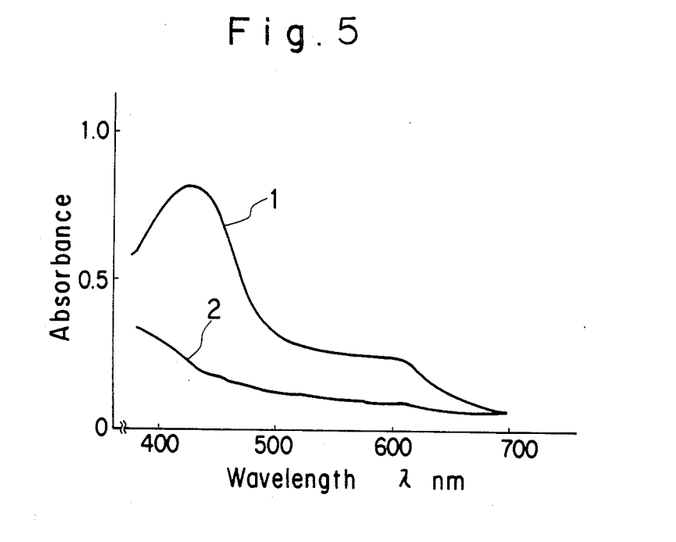

| | | Color developing agent | Color density | Light-fastness (%) | Remarks |
|---|---|---|---|---|---|
| The present invention | Compound No. 1 | 1-(4-octyloxyphenyl)-2-(2'-quinolyl)ethylene | 0.96 | 84.8 | FIG. 1 |
| | Compound No. 6 | 1-(4-methoxyphenyl)-2-(6'-ethoxy-2'-quinolyl)ethylene | 1.01 | 89.1 | FIG. 2 |
| Conventional agents | Comparative Compound No. 1 | 1-(indol-3-yl)-2-(2'-quinolyl)ethylene | 0.81 | 70.3 | FIG. 3 |
| | Comparative Compound No. 2 | 1-(2-methylindol-3-yl)-2-(2'-quinolyl)ethylene | 0.60 | 66.9 | FIG. 4 |
| | Comparative Compound No. 3 | 1-(fran-3-yl)-2-(2'-quinolyl)ethylene | 0.82 | 26.8 | FIG. 5 |

The color density and lightfastness are measured by the following test methods.

(1) Color Density of Developed Color

A solution of 0.06 g of the specimen dissolved in 1.94 g of KMC (a solvent for preparing pressure-sensitive copying paper of alkylnaphthalene series, made by KUREHA Chem. Ind. Co., Japan) is coated on a sheet of ordinary paper by a knife. After piling the painted sheet on a sheet of base paper painted with clay, the piled sheets are passed between rolls to develop a color.

The light absorption of the developed color image is measured by using a spectrophotometer provided with an integrating apparatus (made by SHIMADZU SEISAKUSHO Co., Model UV-200) to obtain a curve 1 of color density of the developed color as shown in FIGS. 1 to 5 in which the wave length is taken in the abscissa and the value of absorption is taken in the ordinate.

(2) Lightfastness

After exposing the developed color image to direct sunlight for 4 hours, the light absorption of the exposed color image is measured by the same spectrophotometer to obtain a curve 2 of color density of the exposed color as shown also in FIGS. 1 to 5. The lightfastness is calculated by the following formula:

Lightfastness (%) =

$$\frac{\text{Absorption value on Curve 2 at the wave length of the adsorption maximum on Curve 1}}{\text{Maximum absorption value on Curve 1}} \times 100$$

As an easy test method, the extent of the color density of developed color and of the lightfastness of a specimen can be clearly estimated by observing the developed color image with naked eyes just after color-development and then also by observing the color image after exposing the developed color image to direct sunlight for 4 hours with naked eyes.

In general, a specimen of color-developing agent giving a density of developed color of larger than about 0.8 and a lightfastness of larger than about 70% in the test methods by using spectrophotometer may be favourable in both the properties.

The compounds of the present invention of the formula (I) can be synthesized by the following method.

A derivative of quinaldine of the formula (II) is brought into condensation with an aldehyde of the formula (III) by using, if necessary, a dehydrating agent such as acetic anhydride and zinc chloride.

$(R^1)_m$— quinaldine —$CH_3$ +

(II)

$(R^2)_n$

OHC— —$OR^3$  $\xrightarrow{\text{Condensation by dehydration}}$ (III)

$(R^1)_m$— quinoline —CH=CH— —$OR^3$ $(R^2)_n$ (I)

wherein $R^1, R^2, R^3$, m and n are the same meanings as defined previously.

On preparing the pressure-sensitive copying paper while using the compounds of the present invention, any public known methods are applicable. For instance, a method by coacervation such as the method disclosed in U.S. Pat. No. 2,806,457 and No. 2,800,458 may be adopted. In addition, on preparing the heat-sensitive recording paper, for instance, the method disclosed in Japanese Patent Publication No. 14039/1970 may be adopted.

Further, the microcapsules containing the compound of the present invention may be coated on the same surface of the paper coated with the electron-accepting substance and, on the other hand, the microcapsules may be coated on the different paper from the coated paper with the electron-accepting substance.

The microcapsules are capable of being ruptured by pressure and the compound of the present invention is developed by the electron-accepting substance when the microcapsules is ruptured and the compound contained therein is brought into contact with the electron-accepting substance which may be coated on the same surface or on the surface of different paper from the coated paper with microcapsules. As an electron-accepting substance according to the present invention, an organic acid, acid clay, activated clay, phenol-formaldehyde resin, a metal salt of aromatic carboxylic acid and aromatic hydroxy compounds such as Bisphenol A may be exemplified.

As a binder according to the present invention, polyvinyl alcohol polyacrylic acid, hydroxyethyl cellulose, methyl cellulose, carboxymethyl cellulose, polyacrylamide, polyvinyl pyrolidone, gelatin and starch may be exemplified.

Preferable compounds of the present invention as a color former are
1-(4-dodecyloxyphenyl)-2-(2'-quinolyl)ethylene,
1-(3-methoxy-4-octyloxyphenyl)-2-(2'-quinolyl)ethylene,
1-(3-methoxy-4-dodecyloxyphenyl)-2-(2'-quinolyl)ethylene,
1-(4-nonyloxyphenyl)-2-(2'-quinolyl)ethylene,
1-(4-decyloxyphenyl)-2-(2'-quinolyl)ethylene,
1-(4undecyloxyphenyl)-2-(2'-quinolyl)ethylene,
1-(3-methoxy-4-nonyloxyphenyl)-2-(2'-quinolyl)ethylene,
1-(3-methoxy-4-decyloxyphenyl)-2-(2'-quinolyl)ethylene,
1-(3-methoxy-4-undecyloxyphenyl)-2-(2'-quinolyl)ethylene,
1-(4-octyloxyphenyl)-2-(6'-ethoxy-2'-quinolyl)ethylene,
1-(4-nonyloxyphenyl)-2-(6'-ethoxy-2'-quinolyl)ethylene,
1-(4-decyloxyphenyl)-2-(6'-ethoxy-2'-quinolyl)ethylene,
1-(4-undecyloxyphenyl)-2-(6'-ethoxy-2'-quinolyl)ethylene,
1-(4-dodecyloxyphenyl)-2-(6'-ethoxy-2'-quinolyl)ethylene,
1-(3-methoxy-4-octyloxyphenyl)-2-(6'-ethoxy-2'-quinolyl)ethylene,
1-(3-methoxy-4-nonyloxyphenyl)-2-(6'-ethoxy-2'-quinolyl)ethylene,
1-(3-methoxy-4-decyloxyphenyl)-2-(6'-ethoxy-2'-quinolyl)ethylene,
1-(3-methoxy-4-undecyloxyphenyl)-2-(6'-ethoxy-2'-quinolyl)ethylene
and 1-(3-methoxy-4-dodecyloxyphenyl)-2-(6'-ethoxy-2'-quinolyl)ethylene.

The present invention will be explained more in detail while referring to the following non-limitative examples.

EXAMPLE 1

Synthesis of 1-(4-octoxyphenyl)-2-(2'-quinolyl)ethylene (Compound No. 1)

A mixture of 7.15 g of quinaldine, 11.7 g of 4-octyloxybenzaldehyde and 20 ml of acetic anhydride was heated under reflux condition for 5 hours. Thereafter, the reaction mixture was introduced into a mixture of 60 ml of aqueous 28% solution of ammonia to neutralize the reaction mixture. Then, the formed solid material was collected by filtering and washed with water. A paste-like product was obtained. After dispersing the paste-like product in 150 ml of toluene, the mixture was heated to dissolve the dispersed product in toluene. After collecting the toluene layer, the toluene solution was cooled to precipitate crystals. After collecting the crystals from the mixture, the collected crystals were dried and then, 17 g of grayish white crystals melting at 95° to 103° C. was obtained as an object compound No. 1 represented by the formula:

The compound No. 1 shows an absorption maximum at 408 nm in 95% acetic acid. The solutions of the compound No. 1 in toluene is colorless. The compound No. 1 develops into yellow color rapidly when the compound No. 1 is brought into contact with silica gel. The elementary analytical data of the compound No. 1 are as follows:

|  | C (%) | H (%) | N (%) |
|---|---|---|---|
| Found: | 83.30 | 8.01 | 4.00 |
| Calcd. as $C_{25}H_{29}NO$: | 83.52 | 8.13 | 3.90 |

EXAMPLE 2

Synthesis of 1-(3-methoxy-4-dodecyloxyphenyl)-2-(2'-quinolyl)ethylene (Compound No. 14)

A mixture of 7.15 g of quinaldine, 16 g of 3-methoxy-4-dodecyloxybenzaldehyde and 20 ml of acetic anhydride was heated under a reflux condition for 5 hours. Thereafter, the reaction mixture was introduced into a mixture of 60 ml of aqueous 28% solution of ammonia to neutralize the reaction mixture. Then, the formed solid material was collected by filtering and washed with water. A paste-like product was obtained. After dispersing the paste-like product in 150 ml of toluene, the mixture was heated to dissolve the dispersed product in toluene. After collecting the toluene layer, the toluene solution was cooled to precipitate crystals. After collecting the crystals from the mixture, the collected crystals were dried and then, 12 g of light yellow crystals melting at 76°–79° C. was obtained as an object compound No. 14 represented by the formula:

The compound No. 14 shows an absorption maximum at 425 nm in 95% acetic acid. The solution of the compound No. 14 in toluene is colorless. The compound No. 14 develops into yellow color rapidly when the compound No. 14 is brought into contact with silica gel. The elementary analytical data of the compound No. 14 are as follows:

|  | C (%) | H (%) | N (%) |
|---|---|---|---|
| Found: | 80.90 | 8.76 | 3.14 |
| Calcd. as $C_{30}H_{39}NO_2$: | 81.03 | 8.81 | 3.11 |

EXAMPLES 3 TO 30

Synthesis of Compound Nos. 2 to 13 and 15 to 30

In the same manner as in Example 1 while changing the combination of quinaldine and 4-methoxybenzaldehyde variously as shown in Table 2, several styryl compounds were synthesized as almost colorless crystals, respectively.

The obtained compounds are shown also in Table 2 together with Compound Nos. 1 and 14. They showed favorable results in the tests of color density of developed color and of lightfastness shown as Table 2.

TABLE 2

| Compound No. | Starting Material | | Product | | | |
|---|---|---|---|---|---|---|
| | Quinaldine derivative | Aldehyde | Structure | Hue | $\lambda_{max}$ (nm)*1 | Melting point (°C.) |
| 1 | [2-methylquinoline structure] | CHO-C6H4-O-n-C8H17 | [quinoline-CH=CH-C6H4-OC8H17] | Yellow | 408 | 95–103 |
| 2 | same as above | CHO-C6H4-OC2H5 | [quinoline-CH=CH-C6H4-OC2H5] | Yellow | 407 | 133–142 |
| 3 | same as above | CHO-C6H4-OC5H11 | [quinoline-CH=CH-C6H4-OC5H11] | Yellow | 408 | 89–93 |
| 4 | same as above | CHO-C6H4-O-C2H4-O-C2H5 | [quinoline-CH=CH-C6H4-OC2H4OC2H5] | Yellow | 405 | 57–65 |

TABLE 2-continued

| Compound No. | Starting Material | | Product | | | |
|---|---|---|---|---|---|---|
| | Quinaldine derivative | Aldehyde | Structure | Hue | λ$_{max}$ (nm)*1 | Melting point (°C.) |
| 5 | same as above | 4-(phenylmethoxy)benzaldehyde (CHO–C₆H₄–O–CH₂–C₆H₅) | Quinoline-CH=CH-C₆H₄-OCH₂-C₆H₅ | Yellow | 406 | 172–180 |
| 6 | 6-ethoxy-2-methylquinoline | 4-methoxybenzaldehyde | 6-C₂H₅O-quinoline-CH=CH-C₆H₄-OCH₃ | Yellow | 407 | 151.5–156 |
| 7 | 2-methylquinoline | 3,5-di-t-butyl-4-hydroxybenzaldehyde | quinoline-CH=CH-(3,5-di-t-Bu-4-OH-C₆H₂) | Yellow | 427 | 135–143 |
| 8 | same as above | 4-(3-chloropropoxy)benzaldehyde | quinoline-CH=CH-C₆H₄-O(CH₂)₃Cl | Yellow | 405 | 81–88 |

TABLE 2-continued

| Compound No. | Starting Material | | Product | | | |
|---|---|---|---|---|---|---|
| | Quinaldine derivative | Aldehyde | Structure | Hue | $\lambda_{max}$ (nm)*1 | Melting point (°C.) |
| 9 | same as above |  |  | Yellow | 396 | 124.5–129 |
| 10 | same as above |  |  | Yellow | 426 | 58–66 |
| 11 |  | (CHO, OCH₃ on benzene) | (quinoline-Cl with CH=CH-C₆H₄-OCH₃) | Yellow | 416 | 177–180.5 |
| 12 | (quinaldine) | (CHO, OC₁₂H₂₅) | (quinoline CH=CH-C₆H₄-OC₁₂H₂₅) | Yellow | 409 | 95–99 |
| 13 | same as above | (CHO, OCH₃, OC₈H₁₇) | (quinoline CH=CH-C₆H₃(OCH₃)(OC₈H₁₇)) | Yellow | 425 | 78.5–80 |

TABLE 2-continued

| | Starting Material | | Product | | | |
|---|---|---|---|---|---|---|
| Compound No. | Quinaldine derivative | Aldehyde | Structure | Hue | $\lambda_{max}$ (nm)*1 | Melting point (°C.) |
| 14 | same as above | CHO-C₆H₃(OCH₃)(OC₁₂H₂₅) | quinoline-CH=CH-C₆H₃(OCH₃)(OC₁₂H₂₅) | Yellow | 425 | 76–79 |
| 15 | same as above | CHO-C₆H₄-O-C₉H₁₉ | quinoline-CH=CH-C₆H₄-OC₉H₁₉ | Yellow | 407 | 95–102 |
| 16 | same as above | CHO-C₆H₄-O-C₁₀H₂₁ | quinoline-CH=CH-C₆H₄-OC₁₀H₂₁ | Yellow | 408 | 96–99 |
| 17 | same as above | CHO-C₆H₄-O-C₁₁H₂₃ | quinoline-CH=CH-C₆H₄-OC₁₁H₂₃ | Yellow | 407 | 96–100 |
| 18 | same as above | CHO-C₆H₃(OCH₃)-O-C₉H₁₉ | quinoline-CH=CH-C₆H₃(OCH₃)(OC₉H₁₉) | Yellow | 426 | 76–81 |

TABLE 2-continued

| | Starting Material | | Product | | | |
|---|---|---|---|---|---|---|
| Compound No. | Quinaldine derivative | Aldehyde | Structure | Hue | $\lambda_{max}$ (nm)*1 | Melting point (°C.) |
| 19 | same as above | CHO-C₆H₃(OCH₃)(OC₁₀H₂₁) | quinaldine-CH=CH-C₆H₃(OCH₃)(OC₁₀H₂₁) with C₂H₅O on quinoline | Yellow | 425 | 77–80 |
| 20 | same as above | CHO-C₆H₃(OCH₃)(OC₁₁H₂₃) | quinaldine-CH=CH-C₆H₃(OCH₃)(OC₁₁H₂₃) | Yellow | 425 | 76–81 |
| 21 | C₂H₅O-quinaldine (with CH₃) | CHO-C₆H₄-OC₈H₁₇ | C₂H₅O-quinoline-CH=CH-C₆H₄-OC₈H₁₇ | Yellow | 407 | 119–125 |
| 22 | same as above | CHO-C₆H₄-OC₉H₁₉ | C₂H₅O-quinoline-CH=CH-C₆H₄-OC₉H₁₉ | Yellow | 407 | 117–126 |
| 23 | same as above | CHO-C₆H₄-OC₁₀H₂₁ | C₂H₅O-quinoline-CH=CH-C₆H₄-OC₁₀H₂₁ | Yellow | 406 | 117–125 |

TABLE 2-continued

| Compound No. | Starting Material | | Product | | | |
|---|---|---|---|---|---|---|
| | Quinaldine derivative | Aldehyde | Structure | Hue | $\lambda_{max}$ (nm)*1 | Melting point (°C.) |
| 24 | same as above | CHO–C₆H₄–O–C₁₁H₂₃ | C₂H₅O-quinoline-CH=CH-C₆H₄-OC₁₁H₂₃ | Yellow | 406 | 116–124 |
| 25 | same as above | CHO–C₆H₄–O–C₁₂H₂₅ | C₂H₅O-quinoline-CH=CH-C₆H₄-OC₁₂H₂₅ | Yellow | 406 | 116–125 |
| 26 | same as above | CHO–C₆H₃(OCH₃)–O–C₈H₁₇ | C₂H₅O-quinoline-CH=CH-C₆H₃(OCH₃)-OC₈H₁₇ | Yellow | 424 | 111–118 |
| 27 | same as above | CHO–C₆H₃(OCH₃)–O–C₉H₁₉ | C₂H₅O-quinoline-CH=CH-C₆H₃(OCH₃)-OC₉H₁₉ | Yellow | 424 | 110–117 |
| 28 | same as above | CHO–C₆H₃(OCH₃)–O–C₁₀H₂₁ | C₂H₅O-quinoline-CH=CH-C₆H₃(OCH₃)-OC₁₀H₂₁ | Yellow | 425 | 110–115 |

TABLE 2-continued

| | Starting Material | | Product | | | |
|---|---|---|---|---|---|---|
| Compound No. | Quinaldine derivative | Aldehyde | Structure | Hue | $\lambda_{max}$ (nm)*[1] | Melting point (°C.) |
| 29 | same as above | 4-(undecyloxy)-3-methoxybenzaldehyde (CHO, OCH₃, OC₁₁H₂₃) | C₂H₅O-quinoline-CH=CH-C₆H₃(OCH₃)(OC₁₁H₂₃) | Yellow | 425 | 108–115 |
| 30 | same as above | 4-(dodecyloxy)-3-methoxybenzaldehyde (CHO, OCH₃, OC₁₂H₂₅) | C₂H₅O-quinoline-CH=CH-C₆H₃(OCH₃)(OC₁₂H₂₅) | Yellow | 425 | 109–116 |

Note:
*[1] Wave length of the absorption maximum (nm)

EXAMPLE 15

Preparation of pressure-sensitive copying paper

Into 94 parts by weight of monoisopropylbiphenyl, was dissolved 6 parts by weight (hereinafter referred to as parts) of 1-(4-octyloxyphenyl)-2-(2'-quinolyl)ethylene of Compound No. 1 prepared in Example 1. The resultant solution was emulsified in a homogenizer by addition of a solution adjusted to pH 7 of 24 parts of gelatin and 24 parts of gum arabic in 400 parts of water. The prepared emulsion was stirred at a temperature of 50° C. for 30 minutes with 1000 parts of warm water added thereto and thereafter, about 1 part of aqueous 10% solution of sodium hydroxide was added to the emulsion and then, the added emulsion was stirred at a temperature of 50° C. for 30 minutes. Subsequently, the resultant emulsion was adjusted to pH 4.5 by gradual addition of dilute acetic acid solution, the adjusted emulsion was stirred at a temperature of 50° C. for about 1 hour and then, stirred further at a temperature of 0° to 5° C. for 30 minutes. Into the emulsion, was gradually added 35 parts of aqueous 4% solution of glutaric dialdehyde to harden the capsules and then, the resultant mixture was adjusted to pH 6 by addition of diluted aqueous solution of sodium hydroxide and thereafter, the adjusted mixture was stirred at a room temperature for a few hours to complete the capsuling step. The liquid mixture including the prepared capsules containing 1-(4-octyloxyphenyl)-2-(2'-quinolyl)ethylene was coated onto a sheet of paper and then, the coated sheet of paper was dried to prepare an upper sheet of paper. The prepared upper sheet of paper was piled on a sheet of paper (as a lower sheet of paper) coated with a phenol-formaldehyde resin as an electron-accepting substance to prepare a pressure-sensitive copying paper. When the prepared pressure-sensitive recording paper was exposed to the pressure applied by the tip of a ball-point pen or to the impact exerted by the types of a typewriter, an image of a deep yellow color appeared on the lower sheet of paper. The colored image showed an excellent lightfastness. In addition, the upper sheet of paper, which is coated with the capsules, also showed an excellent lightfastness without any coloring and reduction of color-developing performance.

EXAMPLE 16

Preparation of pressure-sensitive copying paper

Into 94 parts of monoisopropylbiphenyl, was dissolved 6 parts of 1-(3-methoxyl-4-dodecyloxyphenyl)-2-(2'-quinolyl)ethylene of Compound No. 14 prepared in Example 2. The resultant solution was emulsified in a homogenizer by addition of a solution adjusted to pH 7 of 24 parts of gelatin and 24 parts of gum arabic in 400 parts of water. The prepared emulsion was stirred at a temperature of 50° C. for 30 minutes with 1000 parts of warm water added thereto and thereafter, about 1 part of aqueous 10% solution of sodium hydroxide was added to the emulsion and then, the added emulsion was stirred at a temperature of 50° C. for 30 minutes. Subsequently, the resultant emulsion was adjusted to pH 4.5 by gradual addition of dilute acetic acid solution, the adjusted emulsion was stirred at a temperature of 50° C. for about 1 hour and then, stirred further at a temperature of 0° to 5° C. for 30 minutes. Into the emulsion, was gradually added 35 parts of aqueous 4% solution of glutaric dialdehyde to harden the capsules and then, the resultant mixture was adjusted to pH 6 by addition of a diluted aqueous solution of sodium hydroxide and thereafter, the adjusted mixture was stirred at a room temperature for a few hours to complete the capsuling step.

The liquid mixture including the prepared capsules containing 1-(3-methoxy-4-dodecyloxyphenyl)-2-(2'-quinolyl)ethylene was coated onto a sheet of paper and then, the painted sheet of paper was dried to prepare an upper sheet of paper. The prepared upper sheet of paper was piled on a sheet of paper (as a lower sheet of paper) coated with a phenol-formaldehyde resin as an electron-accepting substance to prepare a pressure-sensitive recording paper. When the prepared pressure-sensitive copying paper was exposed to the pressure applied by the tip of a ball-point pen or to the impact exerted by the types of a typewriter, an image of a deep yellow color appeared on the lower sheet of paper. The colored image showed an excellent lightfastness. In addition, the upper sheet of paper, which is painted with the capsules, also showed an excellent lightfastness without any coloring and reduction of color-developing performance.

EXAMPLE 17

Preparation of heat-sensitive recording paper

In a ball mill, 30 parts of 1-(4-ethoxyphenyl)-2-(2'-quinolyl)ethylene of Compound No. 2 were mixed and pulverized with 150 parts of aqueous 10% solution of polyvinyl alcohol and 65 parts of water to prepare Component A. The particle diameter of the pulverized 1-(4-ethoxyphenyl)-2-(2'-quinolyl)ethylene was 1 to 3 micrometers.

Separately, 35 parts of bisphenol A were similarly mixed and pulverized with 150 parts of aqueous 10% solution of polyvinyl alcohol and 65 parts of water in a ball mill until the particle diameter of the pulverized bisphenol A became 1 to 3 micrometers to prepare Component B. A mixture of 3 parts of Component A and 67 parts of Component B was prepared and the prepared mixture was coated on a sheet of paper and then, the coated sheet of paper was dried. A sheet of heat-sensitive recording paper was obtained with the coated amount of about 5 g/m² in dry base. The obtained sheet of heat-sensitive recording paper rapidly developed a yellow image by heating with a heated pen. The colored image showed a strong resistance to light and moisture.

What is claimed is:

1. A chromogenic compound of the formula:

wherein
R¹ and R² respectively represent a hydrogen atom or a lower alkoxy group of 1 to 5 carbon atoms, R³ represents an alkyl group of 8 to 12 carbon atoms, and m and n are 1.

2. A chromogenic compound according to claim 1, selected from the group consisting of:
1-(3-methoxy-4-octyloxyphenyl)-2-(2'-quinolyl)ethylene,
1-(3-methoxy-4-nonyloxyphenyl)-2-(2'-quinolyl)ethylene,
1-(3-methoxy-4-decyloxyphenyl)-2-(2'-quinolyl)ethylene,
1-(3-methoxy-4-undecyloxphenyl)-2-(2'-quinolyl)ethylene, and
1-(3-methoxy-4-dodecyloxyphenyl)-2-(2'-quinolyl)ethylene.

* * * * *